July 31, 1956 C. V. BENJAMIN Plant Pat. 1,503
PEACH TREE
Filed July 20, 1955
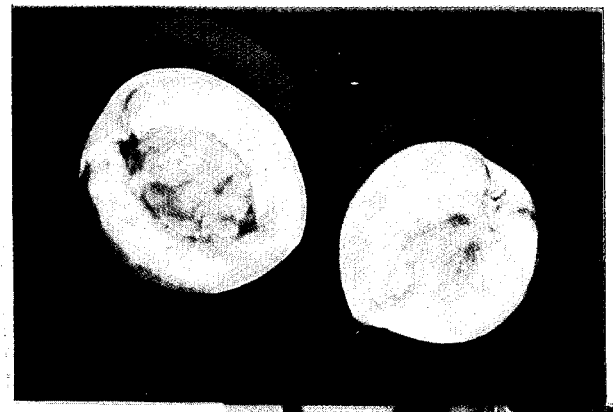
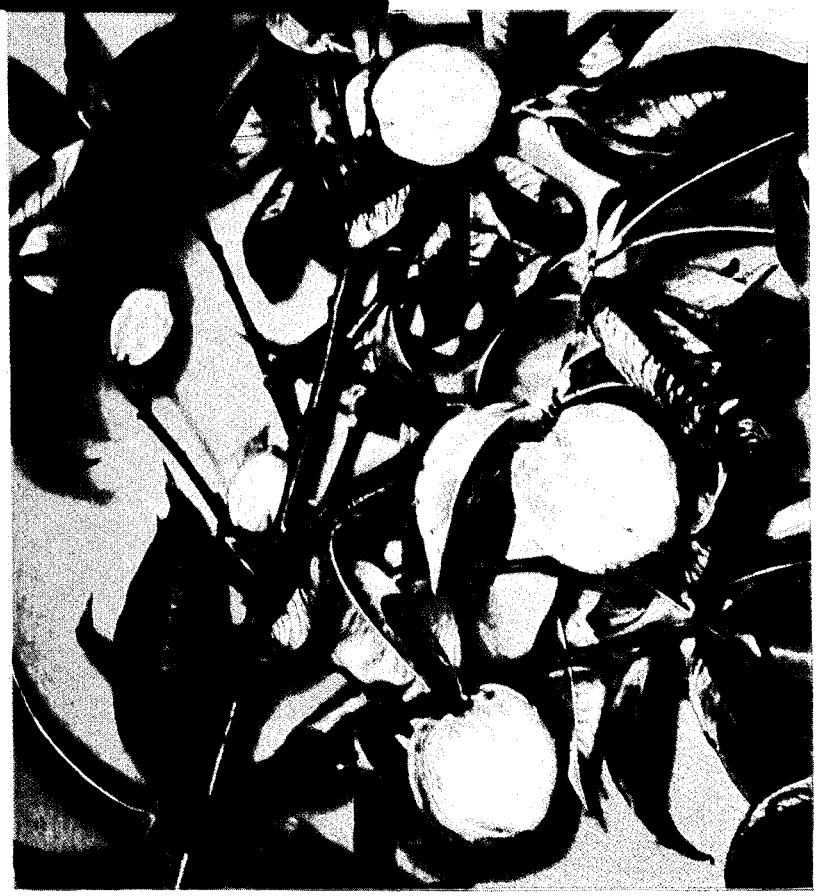
Inventor
C. V. Benjamin
By: Robb & Robb
Attorneys United States Patent Office Plant Pat. 1,503
Patented July 31, 1956

1,503

PEACH TREE

Clara V. Benjamin, Dayton, Ohio, assignor to Harry E. Malter, Monroe, Mich.

Application July 20, 1955, Serial No. 523,400

1 Claim. (Cl. 47—62)

The present invention relates to a new and distinct variety of peach tree of the yellow-fleshed, freestone fruit-bearing class, which was originated by me from a cultivated seed of unknown origin, said seed having been taken from some fruit that was being used domestically. The seedling resulting therefrom particularly attracted my attention because of the fact that it appeared to be endowed with a rather extraordinary and unusal habit of fruit development and ripening in at least three and sometimes four separate and distinct periods ranging from late July to late September in the region of Ohio and southern Michigan.

Continued observations of the new seedling over a prolonged period of years showed that the unique habit referred to above persisted from year-to-year, and further tests and observations based on asexual reproductions of the original seedling, as performed by budding at Monroe, Michigan, have demonstrated and confirmed that this unique habit comes true to form and is established and transmissible through succeeding propagations.

Aside from the unusual habit hereinbefore referred to, which is the most outstanding characteristic and is quite important from a commercial standpoint because of the ability of the variety to prolong the fruiting season substantially beyond the normal range of all other peach varieties of which I am aware, my new variety is further characterized by the desirable size, good appearance and high quality of flavor of its fruit, thus enhancing its value for commercial as well as domestic use.

The accompanying drawing shows in black-and-white typical specimens of the foliage and fruit of my new variety in different stages of development, and further shows in color an enlarged sectional view through a typical fruit specimen, with the stone seated in one half-section and with the cavity exposed in the other half-section, the colors in the latter view being depicted as nearly true as it is reasonably possible to make the same in a color illustration of this character.

The following is a detailed description of my new variety, with color terminology in accordance with the Horticultural Colour Chart issued by The British Colour Council in collaboration with The Royal Horticultural Society, except where general color terms of ordinary dictionary significance are obvious, said description being based upon specimens grown and observed at Monroe, Michigan:

Dates first and last picking: July 20–September 25.

Tree: Medium size; medium vigorous; spreading; dense; rounded; hardy; very productive; regular bearer.

*Trunk.*—Medium stockiness; medium smoothness.

*Branches.*—Medium smoothness; dull. Color—brown.

*Lenticels.*—Medium number; medium size.

*Leaves.*—Size—medium. Length—from 4 inches to 4½ inches; width—from 2¼ inches to 2½ inches. Shape—lanceolate; acutely pointed.

Texture—medium thickness; smooth.

Color—medium green.

Margin—finely serrate.

Petiole—short; thick.

Glands—from 1 to 5 in number, but averaging 3; alternate; medium size; mixed; positioned at points of serration at base of leaf. Color—green.

Stipules—approximately ½ inch in length; roughly toothed. Color—some green and some pink.

Flower buds: Half-hardy; plump; pubescent; short.

Flowers:

*Dates first and full bloom.*—April 10–April 17; medium blooming period as compared with other varieties.

*Size.*—Small.

*Color.*—Pink.

Fruit:

*Maturity when described.*—Under ripe. Date—first crop ripens about August 5; second crop ripens about two weeks after first; third crop ripens about ten days to two weeks after second; fourth crop ripens still later if weather is favorable; successive crops are always substantially equal to or the equivalent of the quality of the first crop in respect to richness of flavor and color of the flesh of the fruit, but sometimes the size of the fruit of the later crops is smaller than that of the first crop when there is a shortage of rainfall and excessive heat during development of the later crops.

*Size.*—Variable. Axial diameter—about 3¼ inches. Transverse diameter in suture plane—about 3 inches. Diameter at right angles to suture plane—about 2¾ inches.

*Form.*—Uniform; symmetrical; globose.

*Suture.*—Distinct; shallow; discontinues at apex.

*Ventral surface.*—Lips—equal.

*Cavity.*—Rounded; with suture showing on one side.

Depth—about ¼ inch.

Breadth—about ¾ inch.

*Base.*—Rounded.

*Apex.*—Short.

*Pistil point.*—Apical.

*Stem.*—About ⅛ inch in length; stout; glabrous; medium adherence to stone.

*Skin.*—Medium thickness; medium tenderness; free. Tendency to crack—slight in wet weather. Color—Buttercup Yellow, Plate 5/1, shading through Orange Buff, Plate 507/2 to Delft Rose, Plate 020/2. Down—moderate; short; does not roll up when rubbed.

*Flesh.*—Color—yellow, with reddish tinge. Surface of pit cavity—color—Buttercup Yellow, Plate 5, shading to Orange Buff, Plate 507/1, and mottled with red next to skin.

Amygdalin—scant.

Juice—rich; watery.

Texture—medium firmness; meaty; melting.

Fibres—fine; tender.

Ripens—evenly.

Aroma—distinct.

Eating quality—good.

Stone: Free.

*Size.*—Medium.

Length—about 1½ inches.

Breadth—about 1 inch.

Thickness—about ¾ inch.

*Form.*—Globose toward apex.

*Sides.*—Equal.

*Surface.*—Irregularly furrowed.

*Ridges.*—Rounded toward base.
*Pits.*—Elongated.
*Ventral edge.*—Thin; without wing.
*Dorsal edge.*—Full.
*Color.*—Currant Red, Plate 821.
*Tendency to split.*—Slight in wet weather.
Use: Local; dessert; culinary.
Keeping quality: Good.
Shipping quality: Medium.
Disease resistance: Has shown no susceptibility to virus diseases, and has never required spraying for foliage or fruit protection, as compared with other varieties grown under comparable cultural conditions at Monroe, Michigan.

I claim:

A new and distinct variety of peach tree of the yellow-fleshed, freestone fruit-bearing class, substantially as herein shown and described, characterized particularly as to novelty by the habit of development and ripening of its fruit in at least three, and sometimes four, separate and distinct periods ranging from late July to late September.

No references cited.